United States Patent [19]

Wehrenberg

[11] Patent Number: 5,144,079

[45] Date of Patent: Sep. 1, 1992

[54] PREPARATION OF TRISUBSTITUTED BENZENE INTERMEDIATES

[75] Inventor: Peter K. Wehrenberg, Oakland, Calif.

[73] Assignee: Imperial Chemical Industries Plc, London, England

[21] Appl. No.: 656,394

[22] Filed: Feb. 14, 1991

[51] Int. Cl.$^5$ ............................................. C07C 315/00
[52] U.S. Cl. ......................................... 568/30; 568/28
[58] Field of Search ............................. 568/30, 32, 28

[56] References Cited

PUBLICATIONS

Ono et al., *Chemistry Letters*, vol. 3, pp. 395-398 (1988).
Mitsunori et al. "The Friedel-Crafts Type Methanesulfonylation of Deactivated Benzenes", *Chemistry Letters*, (1988), pp. 395-398.

*Primary Examiner*—Marianne M. Cintins
*Assistant Examiner*—Margaret Argo
*Attorney, Agent, or Firm*—Edwin H. Baker; Michael J. Bradley

[57] ABSTRACT

This invention relates to a process for the preparation of 2-nitro-4-($C_1$-$C_4$ alkylsulfonyl) toluene or 2-nitro-4-($C_1$-$C_4$ alkylsulfonyl) ethylbenzene by the alkylsulfonylation of 2-nitrotoluene or 2-nitro ethylbenzene.

2 Claims, No Drawings

PREPARATION OF TRISUBSTITUTED BENZENE INTERMEDIATES

This invention relates to a process for the preparation of 2-nitro-4-($C_1$-$C_4$ alkylsulfonyl)toluene or 2-nitro-4-($C_1$-$C_4$ alkylsulfonyl)ethylbenzene by the alkylsulfonylation of 2-nitrotoluene or 2-nitroethylbenzene.

BACKGROUND OF THE INVENTION

A prior art article entitled "The Friedel-Crafts Type Methanesulfonylation of Deactivated Benzenes" by Ono et al, Chemistry Letters, Vol. 3, pp. 395–398 (1988), teaches that the addition of a catalytic amount of trifluoromethanesulfonic acid in an excess of methane sulfonic anhydride is effective for methanesulfonylation of m-dichlorobenzene. The procedure is also taught to be useful for other deactivated benzenes such as p-nitrotoluene in a yield of about 55 percent. A typical procedure involved heating a solution of methanesulfonic acid and thionyl chloride under reflux for one hour to generate the methanesulfonic anhydride, cooling the reaction mixture to 25° C., then adding p-nitrotoluene and trifluoromethane sulfonic acid. The whole mixture is heated to 120° C. for three hours and cooled to 50° C. for recovery of the sulfonylated product by conventional techniques.

Certain 2-(2'4'-disubstituted benzoyl)-1,3-cyclohexanedione herbicides are described in U.S. Pat. No. 4,780,127, issued Oct. 25, 1988, and incorporated herein by reference.

The above-described herbicidal compounds can have the following structural formula

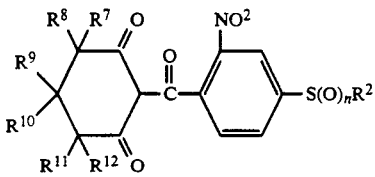

wherein $R^2$ is $C_1$-$C_4$ alkyl and $R^7$ through $R^{12}$ are hydrogen or $C_1$-$C_4$ alkyl.

These herbicides can be prepared by reacting a dione of the structural formula

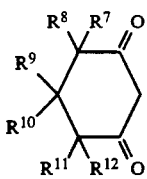

wherein $R^7$ through $R^{12}$ are as defined with a gram molecular weight (mole) of disubstituted benzoyl chloride of the structural formula

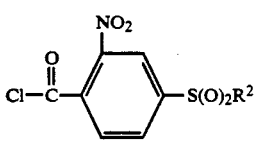

wherein $R^2$ is as defined above. The acid chlorides are readily prepared from the corresponding carboxylic acids by those skilled in the art. In turn, the carboxylic acids may be prepared by oxidation of analogous alkylbenzene according to the formula

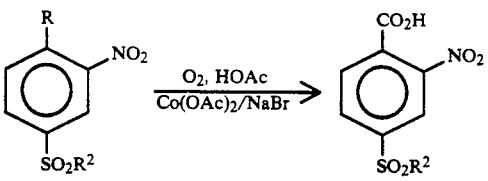

where R is methyl or ethyl and $R^2$ is a $C_1$-$C_4$ alkyl residue. Both steps are taught in U.S. Pat. No. 4,780,127.

SUMMARY OF THE INVENTION

The present invention is directed to a safe, simple, high yield, one-step process for preparing 2-nitro-4-($C_1$-$C_4$ alkylsulfonyl) toluene or 2-nitro-4-($C_1$-$C_4$ alkylsulfonyl) ethylbenzene which has the structural formula

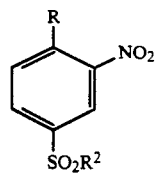

wherein R is methyl or ethyl, preferably methyl, and $R^2$ is $C_1$-$C_4$ alkyl, preferably methyl. The desired methylsulfonylated product is obtained in high yields of over 95 percent.

The process of this invention involves preparing a first mixture of a mole of either 2-nitrotoluene or 2-nitro-ethylbenzene, about 1.0 to about 20.0 moles of a $C_1$-$C_4$ alkyl sulfonic acid and a catalytic amount of catalyst that is useful for the alkyl sulfonylation of a benzene ring. Next, about 1.0 to about 4.0 moles of thionyl chloride are added to the mixture while the mixture is heated to a temperature above about 100° C.

DETAILED DESCRIPTION OF THE INVENTION

The process of this invention involves preparing a mixture of 1.0 mole of either 2-nitrotoluene or, in the alternative, 2-nitroethylbenzene, about 1.0 to about 20.0 moles, preferably about 1.0 to about 10.0 moles and more preferably, about 4.0 to about 10.0 moles of a $C_1$-$C_4$ alkyl sulfonic acid and a catalytic amount of a sulfonylation catalyst. About 1.0 to about 4.0 moles, preferably about 2.0 to 3.0 moles, of thionyl chloride is added, preferably either slowly or portion-wise to the above-described mixture preferably over a 1–4 hour time period. Preferably, the first mixture is heated to a temperature above about 50° C., preferably above about 120° C., more preferably above about 150° C., before the addition of the thionyl chloride. The pre-heating of the mixture and the slow addition of the thionyl chloride are done to insure a safe reaction, but chemically are not necessary.

The resulting mixture is heated to a temperature above about 100° C., preferably above about 120° C., and preferably below a maximum temperature of about 250° C. The higher temperatures can be used by utilizing pressurized reaction equipment.

Alkyl sulfonylation catalysts useful in this invention are as follows: Boric acid; boric anhydride; trifluoromethane sulfonic acid; sulfuric acid on zirconium oxide; titanium tetrachloride, Nafion ® (a polymeric form of trifluoromethane sulfonic acid sold by duPont) and a catalyst called EPZG (sold by Austin Chemical Company). Preferred catalysts are boric acid and boric anhydride, and trifluoromethane sulfonic acid.

At temperatures above about 100° C., 2 moles of $C_1$–$C_4$ alkylsulfonic acid and 1 mole of thionyl chloride react to form an anhydride of the formula $(R^2SO_2)_2O$ where $R^2$ is $C_1$–$C_4$ alkyl, preferably methyl. This reaction is as follows:

$$2R^2SO_3H + SOCl_2 \rightarrow (R^2SO_2)_2O + SO_2 + 2HCl$$

At temperatures above about 120° C., the anhydride will alkylsulfonylate the benzene ring of the 2-nitrotoluene or 2-nitroethylbenzene according to the following reaction scheme:

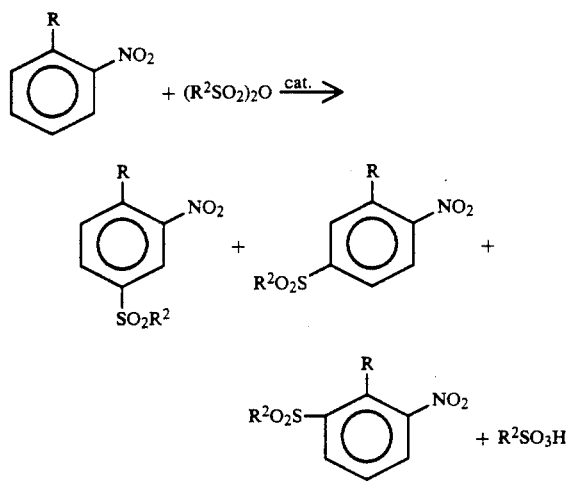

wherein R is methyl or ethyl and $R^2$ is $C_1$–$C_4$ alkyl, preferably methyl.

In the above alkylsulfonylation reaction, the 2-nitro-4-($C_1$–$C_4$ alkylsulfonyl) toluene (ethylbenzene) isomer is formed in a large proportion compared to the 5- and 6-alkylsulfonylated isomers. The 4-substituted isomer is obtained in an amount of 85–95 percent of the total weight of all three isomers.

The 4-substituted isomer can be easily separated from the 5- and 6-substituted isomers by conventional techniques. For example, the desired 4-($C_1$–$C_4$ alkylsulfonyl) isomer can be separated in high yields from the 5- and 6-substituted isomers by crystallization from a solvent such as methylene chloride. The 5- and 6-($C_1$–$C_4$ alkylsulfonyl) isomers remain in solution.

Also in the above reaction scheme, it can be seen that one mole of thionyl chloride is needed to generate one mole of alkylsulfonic anhydride which, in turn, can alkylsulfonylate one mole of 2-nitrotoluene or 2-nitroethylbenzene and that one mole of alkyl sulfonic acid is produced by the reaction. However, as can be seen in Examples I, II, III and V, even when 2moles of thionyl chloride are used (as in the prior art), the 2-nitrotoluene or 2-nitroethylbenzene is not fully consumed. Preferably, about 0.5 to about 2.0 moles of additional thionyl chloride is needed in the process of this invention to produce additional alkyl sulfonic acid anhydride. As can be seen clearly in Example V, this additional thionyl chloride brings about essentially complete conversion of the 2-nitrotoluene or 2-nitroethylbenzene. Furthermore, since the ($C_1$–$C_4$ alkyl)sulfonic acid anhydride is generated and used in situ in this procedure, there is no need to cool the reaction mixture to 20° C., add the thionyl chloride, heat to 120° C. for 1 hour to generate the alkylsulfonic anhydride and finally heat the reaction to affect alkylsulfonylation, as in the prior art.

The following examples illustrate the advantages and superior high yield of the desired products according to the process of this invention as compared to the teaching of the prior art.

EXAMPLE I

Preparation of 4-Methylsulfonyl-2-nitrotoluene Following the Literature Procedure[a]

A mixture of 32.5 milliliters (ml) (0.5 mole) $CH_3SO_3H$ and 14.5 ml (0.2 mole) $SOCl_2$ was heated to reflux while the pot temperature climbed to 120° C. Off gassing was observed. The reaction was cooled to 20° C. and 11.8 ml (0.1 mole) 2-nitrotoluene and 0.9 ml (0.01 mole) $CF_3SO_3H$ were added. The mixture was heated to 120° C. The reaction was monitored periodically on a Hewlett-Packard Model 5890 gas chromatograph (GC). After 6 hours, the reaction showed 35% conversion by GC. GC analysis indicated that after 12 hours, the reaction had stopped with 79% conversion to a mixture of 8% 6-methylsulfonyl-2-nitrotoluene, and 69% 4-methylsulfonyl-2-nitrotoluene along with 21% unreacted 2-nitrotoluene. The reaction mixture was then partitioned between ice water and methylene chloride. The organics were dried over $MgSO_4$, filtered, and stripped to give 22.6 grams (g) of brown oil which crystallized. Infrared, mass and nuclear spectroscopic analysis indicated a mixture of 2-nitrotoluene, 6-methylsulfonyl-2-nitrotoluene, and 4-methylsulfonyl-2-nitrotoluene was obtained in the crystallized reaction product.

[a] "The Friedel-Crafts Type Methanesulfonylation of Deactivation Benzenes" by Ono et al, Chemistry Letters, Vol. 3, pp. 395-398 (1988).

EXAMPLE II

Preparation of 4-Methylsulfonyl-2-nitrotoluene at a Higher Temperature

The reaction procedure of Example I was repeated except that after the addition of the 2-nitrotoluene and $CF_3SO_3H$, the reaction was heated to 160° C. After 15 minutes, GC analysis indicated the presence in the reaction mixture of 68% 2-nitrotoluene, 3% 6-methylsulfonyl-2-nitrotoluene, and 28% 4-methylsulfonyl-2-nitrotoluene. GC analysis indicated that after 6 hours, the reaction had stopped with 92% conversion to a mixture of 8% 2-nitrotoluene, 9% 6-methylsulfonyl-2-nitrotoluene, and 81% 4-methylsulfonyl-2nitrotoluene in the reaction mixture.

EXAMPLE III

Preparation of 4-Methylsulfonyl-2-nitrotoluene with $B_2O_3$ Catalyst

A solution of 65 ml (1.0 mole) $CH_3SO_3H$ and 29 ml (0.4 mole) $SOCl_2$ was heated at reflux until the pot temperature rose to 120° C. (off-gassing) and then was cooled and 23.6 ml (0.2 mole) of 2-nitrotoluene was added. To a 5.0 ml portion of this was added 0.07 g (0.001 mole) boric acid ($B_2O_3$). The reaction mixture was heated in an oil bath at 170° C. for 15 minutes. GC analysis indicated the presence of 42% 2-nitrotoluene, 6% 6-methylsulfonyl-2-nitrotoluene, and 48% 4-methylsulfonyl-2-nitrotoluene.

The reaction procedure of Example III was repeated except that the following catalysts were substituted for $B_2O_3$: Nafion $H^+$(duPont), $H_2SO_4$ on ZrO, and EPZG (Austin Chemical Co.). Conversions of 2 to 10% were obtained with similar product distributions.

The reaction procedure of Example III was repeated except that the reaction mixture was heated to 120° C. and titanium tetrachloride was used as the catalyst. A 6% conversion was obtained.

EXAMPLE IV

Preparation of 4-Methylsulfonyl-2-nitrotoluene without a Catalyst

The reaction procedure of Example III was repeated except that no catalyst was used. After 1 hour at 160° C. no reaction was observed by GC. After further heating to 205° C. for 15 minutes, no reaction was observed by GC.

EXAMPLE V

Preparation of 4-Methylsulfonyl-2-nitrotoluene

According to the process of this invention: $(CH_3SO_2)_2O$ generated in situ, and additional $SOCl_2$ is used to push the reaction to completion.

A solution of 34.5 ml (0.3 mole) of 2-nitrotoluene, 97.5 ml (1.5 mole) $CH_3SO_3H$ and 2.01 g (0.029 mole) $B_2O_3$ was heated to 155° C. and without lowering the temperature, then 43.5 ml (0.6 mole) of $SOCl_2$ was added over 4 hours. The reaction mixture was heated another 3 hours at a temperature of 155° C. and then analysis by GC indicated 10% 6-methylsulfonyl-2-nitrotoluene and 78% 4-methylsulfonyl-2-nitrotoluene with 7% unreacted 2-nitrotoluene. A further addition of 14.5 ml (0.2 mole) $SOCl_2$ was made over 1.5 hours, followed by 1.5 hours of heating at 155° C. Analysis by GC then indicated 11% 6-methylsulfonyl-2-nitrotoluene, and 86% 4-methylsulfonyl-2-nitrotoluene with only 1% 2-nitrotoluene. The reaction product was worked up as in Example I and gave 53.8 g of brown crystalline solid containing 10% 6-methylsulfonyl-2-nitrotoluene and 78% 4-methylsulfonyl-2-nitrotoluene as determined by GC analysis.

I claim:

1. A process for the preparation of a compound having the structural formula

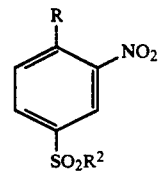

wherein R is methyl or ethyl and $R^2$ is $C_1$–$C_4$ alkyl comprising
   (a) preparing a first mixture of 1.0 mole of 2-nitrotoluene or 2-nitro ethylbenzene, about 1.0 to 20.0 mole of $C_1$–$C_4$ alkyl sulfonic acid and a catalytic amount of boric acid or boric anhydride and
   (b) adding to the first mixture at a temperature above 50° C. about 2.5 to 4.0 moles of thionyl chloride
   (c) heating the resulting mixture at a temperature above about 120° C. to form the desired product.

2. The process of claim 1 wherein R is methyl, $R^2$ is methyl, the catalyst is boric acid and the thionyl chloride is added to the first mixture at a temperature above about 120° C. and the resulting mixture is heated to about 150° C.

* * * * *